(12) United States Patent
Beilfuss et al.

(10) Patent No.: US 6,380,391 B2
(45) Date of Patent: Apr. 30, 2002

(54) PROCESS FOR THE PREPARATION OF BIS(4-AMINO-1-PYRIDINIUM) ALKANES

(75) Inventors: Wolfgang Beilfuss, Hamburg; Ralf Gradtke, Tornesch; Michael Streek, Hamburg, all of (DE)

(73) Assignee: Air Liquide Sante (International), Paris Cedex (FR)

( * ) Notice: Subject to any disclaimer, the term of this patent is extended or adjusted under 35 U.S.C. 154(b) by 0 days.

(21) Appl. No.: 09/779,626

(22) Filed: Feb. 9, 2001

(30) Foreign Application Priority Data

Feb. 10, 2000 (DE) .......................................... 100 05 853

(51) Int. Cl.$^7$ ............................................ C07D 401/02
(52) U.S. Cl. ....................................................... 546/255
(58) Field of Search ................................. 546/257, 255

(56) References Cited

U.S. PATENT DOCUMENTS 4,206,215 A * 6/1980 Bailey ........................ 546/257

FOREIGN PATENT DOCUMENTS

| DE | 27 08 331 | 8/1977 |
| WO | WO 93/24003 | 12/1993 |

OTHER PUBLICATIONS

Bailey et al. "Bispyridinamines: A New Class of Topical Antimicrobiol Agents as Inhibitors of Dental Plaque", XP–002165961, vol. 27, No. 11, 1984, pp. 1457–1464.

* cited by examiner

*Primary Examiner*—Zinna Northington Davis
(74) *Attorney, Agent, or Firm*—Young & Thompson

(57) ABSTRACT

Process for the preparation of bis(4-amino-1-pyridinium) alkanes by reacting difunctionalized alkanes with 4-aminopyridines in water or a mixture of water and organic solvent.

10 Claims, No Drawings

PROCESS FOR THE PREPARATION OF BIS(4-AMINO-1-PYRIDINIUM) ALKANES

The present invention relates to a process for the preparation of bis(4-amino-1-pyridinium)alkanes (BAPA) by reacting difunctionalized alkanes with 4-aminopyridines. The invention further relates to the use in products, in particular body hygiene products, to which the BAPA prepared by the process according to the invention have been added.

U.S. Pat. No. 4,206,215 discloses the preparation of BAPA in inert solvents, such as a lower alkanol, acetonitrile, N,N-dimethylformamide, N,N-dimethylacetamide, benzene, toluene or xylene at a temperature from 80 to 150° C. for a period of from 1 to 24 hours, and also the reaction in the absence of a solvent by heating stoichiometric amounts of the reaction components for from about 2 to 5 hours at 120 to 150° C. Aprotic solvents and similar reaction conditions are described by Bailey et al. in J. Med. Chem. 1984, 27, 1457–64.

However, the known processes for the preparation of BAPA have numerous disadvantages:

1. The use of organic solvents (in the process preferred in the prior art these are toxicologically unacceptable solvents such as acetonitrile, and N,N-dimethylformamide, which is injurious to health, and, in particular, hazardous for reproduction) is associated with particular technical problems during the preparation, e.g. risk of explosion etc.
2. The use of organic solvents increases the preparation costs since the solvents have to be heated, processed and disposed of, all of which require energy.
3. The relatively high reaction temperature promotes the increased formation of byproducts, noticeable from the discoloration of the reaction mixtures during the reaction, and the products resulting therefrom are likewise coloured.
4. These byproducts and also the contaminations with solvents introduced as a result of the obligatory use of toxicologically unacceptable reaction media, have to be removed in purification steps which are costly (in terms of energy). These obligatory purification steps make the known processes less interesting from an economical viewpoint.
5. The use of the high requirements placed on the purity of the BAPA, expensive quality controls have to be carried out in all process steps.
6. If the process is carried out in accordance with the prior art in health-injurious, in particular reproduction-hazardous dimethylformamide, then a yield of, for example, 77% can be achieved (see Example 6).
7. If the reaction is carried out in toxicologically acceptable acetone, then no product can be isolated in a noteworthy amount (see Example 9).
8. The formation of byproducts and the unsatisfactory yield lead to losses of expensive starting materials, starting firstly during the reaction and secondly during purification.

Accordingly, the object of the present invention was to develop a simple process for the preparation of BAPA which does not have the above-mentioned disadvantages. This preparation process should be advantageous particularly from a production efficiency viewpoint. Because BAPA, inter alia, are used in pharmaceutical and body hygiene products etc., and the corresponding specifications have to be satisfied, they must also be free from traces of any toxicologically unacceptable impurity, which can originate, for example, from the solvent used.

Surprisingly this object is achieved by the process according to the invention for the preparation of BAPA which is carried out in the reaction medium of water or a mixture of water and solvent. According to the process of the invention, yields greater than 80%, even greater than 90%, are possible.

The invention relates to process for the preparation of bis(4-amino-1-pyridinium)alkanes of the formula I

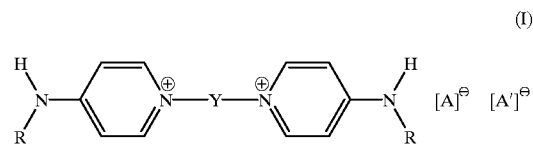

(I)

by reacting difunctionalized alkanes of the general formula II $$A—Y—A'$$ (II), in which Y is a linear or branched alkylene group having 4 to 18 carbon atoms, and A and A' are identical or different and are a reactive functional group,
with 4-aminopyridines of the general formula III

(III)

in which R is linear or branched and is an alkyl, cycloalkyl or alkylaryl group having 5 to 18 carbon atoms,
in a reaction medium and is characterized in that the reaction medium is water or a mixture of water and an organic solvent which comprises at least 10% by weight of water.

Preferred reactive functional groups A and A' are chlorine, bromine, iodine, methanesulphonyloxy, ethanesulphonyloxy, benzenesulphonyloxy or p-toluenesulphonyloxy.

Y is preferably an alkylene group having 6 to 16 carbon atoms, particularly preferably 8 to 14 carbon atoms, for example 10 carbon atoms, such as, for example, a dec-1,10-diyl group.

R is preferably an alkyl, cycloalkyl or alkylaryl group, in particular an alkyl group, having 6 to 15, in particular 8 to 12, carbon atoms, for example an n-octyl group.

The organic solvent of the aqueous reaction medium is chosen from alcohols, glycols, polyols, polyethylene and polypropylene glycols, ethers, glycol mono- and diethers, completely or incompletely etherified polyols and completely or incompletely etherified polyethylene or polypropylene glycols, and mixtures thereof. Preference is given to 1,2-propylene glycol, phenoxypropanols and phenoxyethanol. Particular preference is given to the solvents (or solvent mixtures of) phenoxyethanol, 2-phenoxy-1-propanol and 1-phenoxy-2-propanol. It is, for example, possible to use 2-phenoxy-1-propanol and 1-phenoxy-2-propanol as a mixture, in any desired ratio, preferably 1:100 to 100:1 parts by weight, in particular 30:70 to 99:1 parts by weight, e.g. the commercially available mixture of 85 parts by weight of 2-phenoxy-1-propanol and 15 parts by weight of 1-phenoxy-2-propanol.

The reaction medium of the process according to the invention comprises at least 10% by weight, preferably at least 30% by weight, in particular at least 50% by weight, such as, for example, 70% by weight, and even up to 100% by weight, of water, and accordingly at most 90% by weight, preferably at most 70% by weight, in particular at most 50% by weight, for example 30% by weight, or even down to 0% by weight, of organic solvent. The process according to the invention is advantageous merely because it is not necessary to use any toxicologically unacceptable solvents and, consequently, in the case of the product prepared in accordance with the process of the invention, the removal, even of small amounts, e.g. of less than 1% by weight, of residues of toxicologically acceptable solvents, as is always necessary for the known processes, in order to satisfy the corresponding specifications, is dispensed with.

In a preferred embodiment no organic solvent is present, i.e. the reaction medium is water.

The reaction mixture can further comprise salt, for example potassium chloride or sodium chloride, the addition of salt, as is known, resulting in an increase in the boiling point of the reaction mixture.

The invention further relates to the use of the products prepared by the process according to the invention in an antimicrobial composition, e.g. a body care composition.

The reactants 4-aminopyridine according to formula (III) and difunctionalized alkane according to formula (II) are added to the reaction medium. The resulting reaction mixture preferably comprises at most 80% by weight, in particular at most 65% by weight, e.g. 50% by weight, of reaction medium. In this connection, it is possible for a multiphase system to form, for example a 2-phase system. To increase the rate of the reaction, the reaction product bis(4-amino-1-pyridinium)alkane of the formula I can be added as emulsifier. For a batch size of 0.2 mol of aminopyridine of the formula III, the preferred amount of reaction medium is 5 to 30 ml, in particular 10 to 20 ml, e.g. 15 ml.

The reaction is carried out by heating to 70° C. to 120° C., preferably 80° C. to 110° C., e.g. 100° C., it being possible to carry out the reaction, if desired, under a pressure of from 1 to 20 bar, preferably 2 to 10 bar, e.g. 5 bar, at a temperature which is higher than the boiling temperature of the reaction medium under atmospheric pressure. In a preferred embodiment, the reaction takes place at reflux. In the preferred reaction medium of water (free from organic solvent), the reaction is preferably carried out at the boiling temperature of water, preferably at 100 to 110° C., e.g. at 100° C., at 1 to 10 bar, e.g. at 1 bar or at 5 bar.

It will be appreciated by the person skilled in the art that the starting material 4-aminopyridine of the formula III can also be used in the form of mixtures (in any desired ratio, preferably 1:100 to 100:1) with its respective hydrohalide or in the form of its hydrohalide.

Heating is terminated after 1 to 48 hours, preferably 4 to 20 hours, in particular 6 to 12 hours, for example 8 hours or 10 hours. The progress of the reaction can, if desired, be monitored, for example, by measuring the pH.

During cooling, an amount or a further amount of the solvent according to the invention can, if desired, be added in order to complete precipitation of the product from the reaction medium and thus to increase the yield. Furthermore, as a result, a desired specific crystallization of the product can be achieved if, for example, a particularly coarse- or fine-crystalline form of the product is desired. The person skilled in the art is familiar with these methods for influencing the crystallization. During further processing, losses in yield can arise.

Following cooling to 50° C. or below, preferably less than 45° C., in particular less than 35° C., for example 20° C. or 5° C., the reaction is terminated, and the product is isolated in the usual manner, for example by filtration, if the product is insoluble in the reaction medium, or by dilution of the reaction medium, e.g. with a nonpolar solvent, in order to precipitate out the product, or by evaporation of the reaction medium, in which case the product is left behind as residue. In a preferred embodiment, acetone is added during this cooling phase, preferably at 50° C. or below, particularly preferably at 45 to 35° C., in order to complete the precipitation. The isolated crude product has a high purity, but can, if desired, be further purified by crystallization from a suitable solvent in the presence of an adsorbent, for example activated carbon or diatomaceous earth. If a specific purity of the product BAPA is desired, then it is possible to remove impurities, for example the starting material, in accordance with known processes. In the case of the BAPA obtained by the process of the invention, which is already in the form of a crude product of high purity, the purification can, for example, be carried out by washing with water, for example iced water. A preferred purification method is the simple and repeated recrystallization from acetone/water, by dissolving the crude product according to the invention in a mixture of acetone and water in any desired ratio, preferably 1:10 to 20:1, in particular 5:1 to 15:1, e.g. 10:1, optionally with warming, then cooling the mixture to preferably less than 20° C., in particular, less than 10° C., e.g. 5° C., to precipitate the product, which is filtered off.

The BAPA prepared by the process of the invention are salts containing the anions A and A'. The anionic radical can, if desired, be varied by the known ion exchange methods. These methods for the preparation of soluble and insoluble BAPA containing numerous different anions are known in the prior art, and an overview thereof is given, inter alia, in DE 27 08 331 C2.

It is known to the person skilled in the art that BAPA can be in the form of the pyridinium salts, and also as isomeric salts in the corresponding quinoid limiting structure, and as mixtures thereof.

As is described below, the BAPA have antimicrobial activity towards a variety of species of micro-organisms which include both gram-positive and also gram-negative bacteria, various species of fungi and herpes viruses. The BAPA are therefore suitable for use in antimicrobial and/or antiseptic compositions, which can be applied topically to remove germs from human skin or other tissue, and to antisepticize or to disinfect inanimate surfaces. Thus, the BAPA can be used in topical antiseptic solutions for the treatment of wounds, in antibacterial cleaners, such as surgical handwashes, preoperative skin preparations for patients, soaps and shampoos, or in domestic and industrial cleaners, disinfectants and protective coatings, such as paints, lacquers or varnishes and waxes. The BAPA are rendered suitable for use for the purposes indicated above by combinations with customary diluents or carriers, compatible cationic, anionic or nonionic surfactants, buffers, odourizing agents, and colour-imparting agents, and are applied to the surface to be disinfected in the customary manner, such as, for example, by brushing, spraying, dotting or immersing.

For use as skin cleansers, the BAPA prepared by the process of the invention can be used in liquid formulations or, if desired, the liquid formulations can be thickened by means of specific additives to give a gel or a paste, or moulded according to customary methods to give a stick. For example, the compounds can be formulated with any compatible, pharmaceutically useful surface-active agents, preferably a nonionic surface-active agent, amine oxides, or with mixture thereof. The formulations can additionally comprise pharmaceutically useful diluents, such as, for example, water or $C_1$- to $C_5$-alkanols, acids, bases or buffers in order to keep the pH between 5.0 and 7.5, and optionally perfume and dyes.

The BAPA prepared by the process according to the invention are generally used in such formulations in a concentration up to 20% by weight, preferably 0.05 to 10% by weight, in particular 0.5 to 5% by weight, e.g. 1.0 or 2.0% by weight.

The compounds can also be formulated in suitable pharmaceutical vehicles for the treatment of bacterial, fungal and herpes viral infections, for example as lotions, ointments or creams, by incorporation into customary lotion, ointment or cream base materials, such as alkyl polyether alcohols, cetyl alcohol or stearyl alcohol, or as powders by incorporation into customary powder base materials, such as starch or talc, or as gel by incorporation into customary gel base materials, such as glycerol or tragacanth gum. They can also be formulated for use as aerosol sprays or foams.

In the case of the use for the antisepticizing and disinfection of inanimate surfaces, the compounds can be formulated with known detergents and base materials, such as trisodium phosphate or borax.

The BAPA are effective in preventing the formation of dental plaque. If the BAPA prepared by the process according to the invention are intended for such an application, then they can advantageously be applied to the teeth in the form of a mouth rinse or a dentifrice. The compounds can be formulated with customary constituents which are used in mouth rinses and dentifrice formulations, for example water, alcohols, glycerol, buffers, thickeners, flavourings and colorants.

It goes without saying that the vehicles, diluents, carriers and additives which are present in the above formulations are compatible with BAPA, i.e. that the antibacterial, antifungal and virucidal activity of the BAPA is not impaired by effects attributed to the nature of the vehicle, diluent, carrier or other additive.

Accordingly, the advantages of the process according to the invention are:
cost-effective reaction medium,
toxicologically acceptable reaction medium, the product is therefore automatically free from toxicologically unacceptable solvent residues,
comparatively low reaction temperature,
low formation of byproducts,
economical preparation process, e.g. as a result of lower or no redistillation costs,
favourable ratio of reactants (or reaction product) to reaction medium possible (e.g. a ratio of 1:1), accordingly economical in terms of energy,
high purity and high yield of the product BAPA, which satisfies the specification,
improvement in plant safety (inter alia by reducing the risk of explosion),
high yield to desired product of more than 80%, even of more than 90%, possible, and consequently economical in terms of feed materials.

The examples below illustrate the advantages of the process according to the invention.

EXAMPLE

In the examples below, the term "octenidine dihydrochloride" means N,N'-(decane-1,10-diyldi-1(4H)-pyridyl-4-ylidene)bis(octylammonium)dichloride or its isomer 1,1'-(decan-1,10-diyl)bis[4-(octylamino)pyridinium]dichloride.

Example 1

20.6 g (0.1 mol) of 4-octylaminopyridine, 10.5 g (0.05 mol) of 1,10-dichlorodecane and 30 ml of demineralized water were combined and refluxed with stirring. The initially cloudy, yellowish solution became clear and yellow after 3 hours. After the mass had been stirred for a further hour at reflux, it was cooled to 5° C. The resulting white, semisolid paste was filtered off with suction, and the product octenidine dihydrochloride in the form of colourless crystals was washed with iced water.

Example 2

41.3 g (0.2 mol) of 4-octylaminopyridine, 21.0 g (0.1 mol) of 1,10-dichlorodecane and 15.7 ml of demineralized water were combined and refluxed with stirring. From 45° C. the 4-octylaminopyridine started to melt. The temperature rose to 105° C., and the reaction mass became homogeneous, and the mixture was stirred for 6 hours at 100° C. The clear, slightly yellowish solution was then cooled to 50° C., and 100 ml of acetone were added, giving a clear, slightly yellowish solution, and after a further 170 ml of acetone had been added the mixture was cooled to 5° C. The product was filtered off with suction and washed with ice-cold acetone and dried (colourless crystals, yield 53.4 g, 0.0857 mol, 85.7% of theory, melting point 214–217° C.). The product, having a purity of >99.3%, satisfies the specification.

Example 3

41.3 g (0.2 mol) of 4-octylaminopyridine, 21.0 g (0.1 mol) of 1,10-dichlorodecane and 27.1 ml of demineralized water were combined and refluxed with stirring. From 45° C. the 4-octylaminopyridine started to melt, and after 45 minutes at 100° C. the initially two-phase reaction mixture became single-phase. It was stirred for 6 hours at 100° C., and then the clear yellowish solution was cooled to 50° C., and 270 ml of acetone were added. After cooling to 5° C., the product was filtered off with suction, washed with ice-cold acetone and dried (colourless crystals, 47.1 g, 75.5% of theory, melting point 215–217° C.).

Example 4

20.6 g (0.1 mol) of 4-octylaminopyridine, 10.5 g (0.05 mol) of 1,10-dichlorodecane and 5.5 ml of demineralized water were combined and refluxed for 5 hours with stirring. The clear yellowish solution was cooled slowly, and at about 60° C. the reaction mixture became solid. The addition of 130 ml of acetone and a further 8 ml of demineralized water gave a clear, slightly yellowish solution, which was cooled to 5° C. The product was filtered off with suction and washed with a little ice-cold acetone (colourless crystals, melting point 214–217° C., 26.6 g, corresponds to 85.3% of theory).

Result

The yield to the desired product can be more than 90%. For example, according to Example 2, the further-processed product is present, for a yield of 85.7% of theory, in a purity of >99.3%, and is free from toxicologically unacceptable solvent residues.

Comparative Examples

Example 5

20.6 g (0.1 mol) of 4-octylaminopyridine, 10.5 g (0.05 mol) of 1,10-dichlorodecane and 30 ml of 1,2-propylene glycol were combined and heated to 130° C. The exothermic reaction causes the temperature to rise to 140° C., and the reaction mixture turns pale orange. After stirring the mixture for 3 hours at 135° C., it was cooled to room temperature. No precipitate was obtained from the mixture within 3 days, and after 150 ml of water had been added, a small amount of a pale orange crystalline precipitate was filtered off with suction.

Example 6

20.6 g (0.1 mol) of 4-octylaminopyridine, 10.5 g (0.05 mol) of 1,10-dichlorodecane and 30 ml of N,N-dimethylformamide were combined and heated to 130° C. The exothermic reaction causes the temperature to increase to 140° C., and the mixture turns red. The mixture is stirred for a further 3 hours at 135° C., and during cooling a crystal sludge crystallized from about 90° C., which was filtered off with suction and washed with DMF, giving pale red crystals. The resulting moist crystals (37.1 g) were dissolved from a mixture of acetone (125 ml) and demineralized water (7.5 ml) and, after cooling to 5° C., the product was filtered off with suction and washed with cold acetone (colourless crystals having a purity of 99.1%, 24.1 g, 0.0387 mol, 77.4% of theory).

Example 7

20.6 g (0.1 mol) of 4-octylaminopyridine, 10.5 g (0.05 mol) of 1,10-dichlorodecane and 30 ml of N-methylpyrrolidone were combined and heated to 130° C. The exothermic reaction causes the temperature to increase to 140° C., and the mixture turns deep red. The reaction mass was stirred for a further 3 hours at 135° C., and during cooling a crystal sludge crystallized from about 90° C., which was filtered off with suction and washed with NMP, giving pale red crystals.

Example 8

20.6 g (0.1 mol) of 4-octylaminopyridine, 10.5 g (0.05 mol) of 1,10-dichlorodecane and 30 ml of white spirit (boiling point 155 to 200° C.) were combined and heated to 130° C. The exothermic reaction causes the temperature to increase to 155° C., and at the same time white crystal precipitate out. The reaction mixture was stirred for a further 4 hours at 140° C., and after cooling to room temperature the very fine crystal sludge was filtered over a filterpaper and washed with petroleum ether, giving a beige, solid mass. The reaction product octenidine dihydrochloride in this example is very difficult to filter off with suction since it is produced in very fine form.

Example 9

41.3 g (0.2 mol) of 4-octylaminopyridine, 21.1 g (0.1 mol) of 1,10-dichlorodecane and 250 ml of acetone were combined and refluxed. The initially clear, colourless solution forms small amounts of colourless crystals in yellow solution after 44 h. It is not possible to isolate the product in a noteworthy amount.

Result of the Comparative Examples

The products obtainable by the processes of Comparative Examples 5 to 8 are immediately to be identified in optical terms as of lower purity (they are yellowish, reddish or beige-coloured) and are not pure by a thin layer chromatography (eluent chloroform to methanol—1:1), there is an impurity at $R_f$=0.7 which could not be identified. Products of good purity can be obtained by recrystallization, although the yield then drops to unsatisfactory values. For example, according to Example 6, the product is produced in a purity of 99.1% at a yield of firstly only 77.4%, but, secondly, toxicologically unacceptable, health-injurious, in particular reproduction-hazardous, DMF is still present.

What is claimed is:
1. Process for the preparation of bis[4-amino-1-pyridinium]alkanes of the formula I

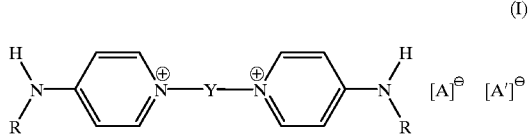

by reacting difunctionalized alkanes of the formula II

in which Y is a linear or branched alkylene group having 4 to 18 carbon atoms, and A and A' are identical or different and are a reactive functional group,
with 4-aminopyridine of the formula III

in which R is linear to branched and is an alkyl, cycloalkyl or alkylaryl group having 5 to 18 carbon atoms,
in a reaction medium, wherein the reaction medium is water or a mixture of water and an organic solvent which comprises at least 10% by weight of water.

2. Process according to claim 1, wherein Y is an alkylene group having 6 to 16 carbon atoms.

3. Process according to claim 2, wherein Y is a dec-1,10-diyl group.

4. Process according to claim 1, wherein R is an alkyl, cycloalkyl or alkylaryl group.

5. Process according to claim 4, wherein R is a n-octyl group.

6. Process according to claim 1, wherein A and A' are chosen from the group consisting of chlorine, bromine, iodine, methanesulphonyloxy, ethanesulphonyloxy, benzenesulphonyloxy or p-toluenesulphonyloxy.

7. Process according to claim 4, wherein A and A' are identical and are chlorine.

8. Process according to claim 1, wherein the solvent is chosen from alcohols, glycols, polyols, polyethylene and polypropylene glycols, ethers, glycol mono- and diethers, completely or incompletely etherified polyols and completely or incompletely etherified polyethylene or propylene glycols, and mixtures thereof.

9. Process according to claim 8, wherein the solvent is chosen from 1,2-propylene glycol, phenoxypropanols and phenoxyethanol, and mixtures thereof.

10. Process according to claim 1, wherein the reaction medium is water.

* * * * *